(12) United States Patent
Stefanyszyn

(10) Patent No.: US 10,278,860 B2
(45) Date of Patent: May 7, 2019

(54) MEDIAL ORBICULARIS FLAP CANTHOPLASTY WITH ORBICULARISORRHAPHY

(71) Applicant: Mary A. Stefanyszyn, Philadelphia, PA (US)

(72) Inventor: Mary A. Stefanyszyn, Philadelphia, PA (US)

(*) Notice: Subject to any disclaimer, the term of this patent is extended or adjusted under 35 U.S.C. 154(b) by 0 days.

(21) Appl. No.: 16/000,360

(22) Filed: Jun. 5, 2018

(65) Prior Publication Data
US 2018/0344522 A1 Dec. 6, 2018

Related U.S. Application Data

(60) Provisional application No. 62/515,222, filed on Jun. 5, 2017.

(51) Int. Cl.
| | | |
|---|---|---|
| *A61F 9/007* | (2006.01) | |
| *A61B 17/28* | (2006.01) | |
| *A61B 17/285* | (2006.01) | |
| *A61B 17/3211* | (2006.01) | |

(52) U.S. Cl.
CPC .......... *A61F 9/00718* (2013.01); *A61B 17/28* (2013.01); *A61B 17/285* (2013.01); *A61B 17/3211* (2013.01)

(58) Field of Classification Search
CPC ... A61B 17/28; A61B 17/285; A61B 17/3211; A61F 9/00718
See application file for complete search history.

(56) References Cited

U.S. PATENT DOCUMENTS 5,830,233 A * 11/1998 Suson .................. A61B 17/08
606/215

OTHER PUBLICATIONS

Sira et al., "Transcaruncular Medical Canthal tendon Plication with Lower Eyelid Suture Sling in Facial Nerve Palsy" The International Journal on Orbital Disorders, Oculoplastic and Lacrimal Surgery, Orbit, vol. 33(3), pp. 159-163, 2014.
Sakamoto et al., "New Technique for Medical Canthoplasty that Incorporates Modified V-W Epicanthoplasty", Arch Facial Plast Surg, vol. 14, No. 1, pp. 56-61, 2012.

(Continued)

*Primary Examiner* — William H Matthews
(74) *Attorney, Agent, or Firm* — Panitch Schwarze Belisario & Nadel LLP

(57) ABSTRACT

A surgical ophthalmic procedure performs a medial canthoplasty of an eyelid system having the following steps: performing a medial subciliary skin incision in the medial inferior-eyelid skin, excising an ellipse of the medial inferior-eyelid skin extending medially upwardly; exposing the medial canthal tendon, creating an orbicularis flap from the inferior-lid orbicularis muscle, suturing the orbicularis flap to the medial canthal tendon, probing the lacrimal system to confirm the integrity of the canalicular system, excising the excess portion of the medial superior-eyelid skin, closing the medial canthal skin with deep fixation in the medial canthus, closing the medial subciliary skin incision or extending the subciliary incision, making a supraciliary skin incision in the upper lid medially and performing an orbicularisorrhaphy by suturing the orbicularis of the upper lid to the orbicularis of the lid to further close the lid.

2 Claims, 11 Drawing Sheets

(56) References Cited

OTHER PUBLICATIONS

Duvall et al., Medical Canthoplasty: Early and delayed Repair, The Laryngoscope, vol . 91, No. 2, pp. 173-183, Feb. 1981.
Sun et al., "Medical Canthoplasty Combined With Conjunctivodacryocystorhinostomy for the treatment of Delayed Medial Telecanthal Deformity" Chinese Medical Journal, vol. 130, Issue 6, pp. 698-702, Mar. 20, 2017.
Howard et al., Medial Canthoplasty With Microplate Fixation Arch Ophthalmol, vol. 110, pp. 1793-1797, Dec. 1992.
Okazaki et al., "Medical Canthoplasty with the Mitek Anchor System", Annals of Plastic Surgery, vol. 38, No. 2, pp. 124-128, Feb. 1997.

\* cited by examiner

MEDIAL ORBICULARIS FLAP CANTHOPLASTY WITH ORBICULARISORRHAPHY

CROSS-REFERENCE TO RELATED APPLICATIONS

This application claims the benefit of U.S. Provisional Patent Application No. 62/515,222, filed Jun. 5, 2017, the disclosure of which is incorporated herein by reference.

BACKGROUND OF THE INVENTION

The present invention relates to a surgical ophthalmic procedure for performing a medial canthoplasty. More particularly, the present invention relates to a surgical oculoplastic procedure for performing a medial orbicularis flap canthoplasty to tighten the medial canthal tendon and may include a medial alternative to a lateral tarsorrhaphy as an option to further close the eye.

Upon aging, the lower eyelid becomes lax and ectropic, a condition in which the eyelid turns outwardly and no longer tight against the globe leaving the inner eyelid surface exposed and prone to irritation, typically resulting in tearing and discomfort. The most common way to surgically correct this condition is a lateral canthal tightening procedure which is relatively easy to perform. The medial aspect of the eyelid may continue to be ectropic in spite of the lateral canthal tightening procedure and is difficult to fix surgically because of the absence of a tarsus medially and the medial presence of the lacrimal drainage system which includes the puncta and the canaliculus.

Numerous medial canthoplasty procedures to correct medial laxity and ectropion have been described in the medical literature. Typically, these procedures use skin flaps in conjunction with lower eyelid lid shortening procedures and tarsal resuspension to the medial canthal tendon; however most medial canthoplasty procedures are difficult and don't achieve the functionally successful result of tightening and lifting the medial eyelid and correcting the ectropion of the medial lid margin and the punctum without damaging the lacrimal drainage system.

If the eyelid is paralyzed or extremely ectopic, lid closure more than provided by a lateral canthal tightening is required to protect the cornea from exposure. Laterally, this is achieved by performing a lateral tarsorrhaphy, which consists of suturing the tarsus of the lower lid to the tarsus of the upper lid. Medially, suturing the tarsi together is not possible as each tarsus ends at the puncta and is not present medial to the puncta.

For the foregoing reasons, there is a need for a surgical ophthalmic procedure for performing a medial orbicularis flap canthoplasty to tighten the medial canthal tendon and which provides a medial alternative to a lateral tarsorrhaphy as an option for further close of the eye.

BRIEF DESCRIPTION OF THE SEVERAL VIEWS OF THE DRAWINGS

The following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
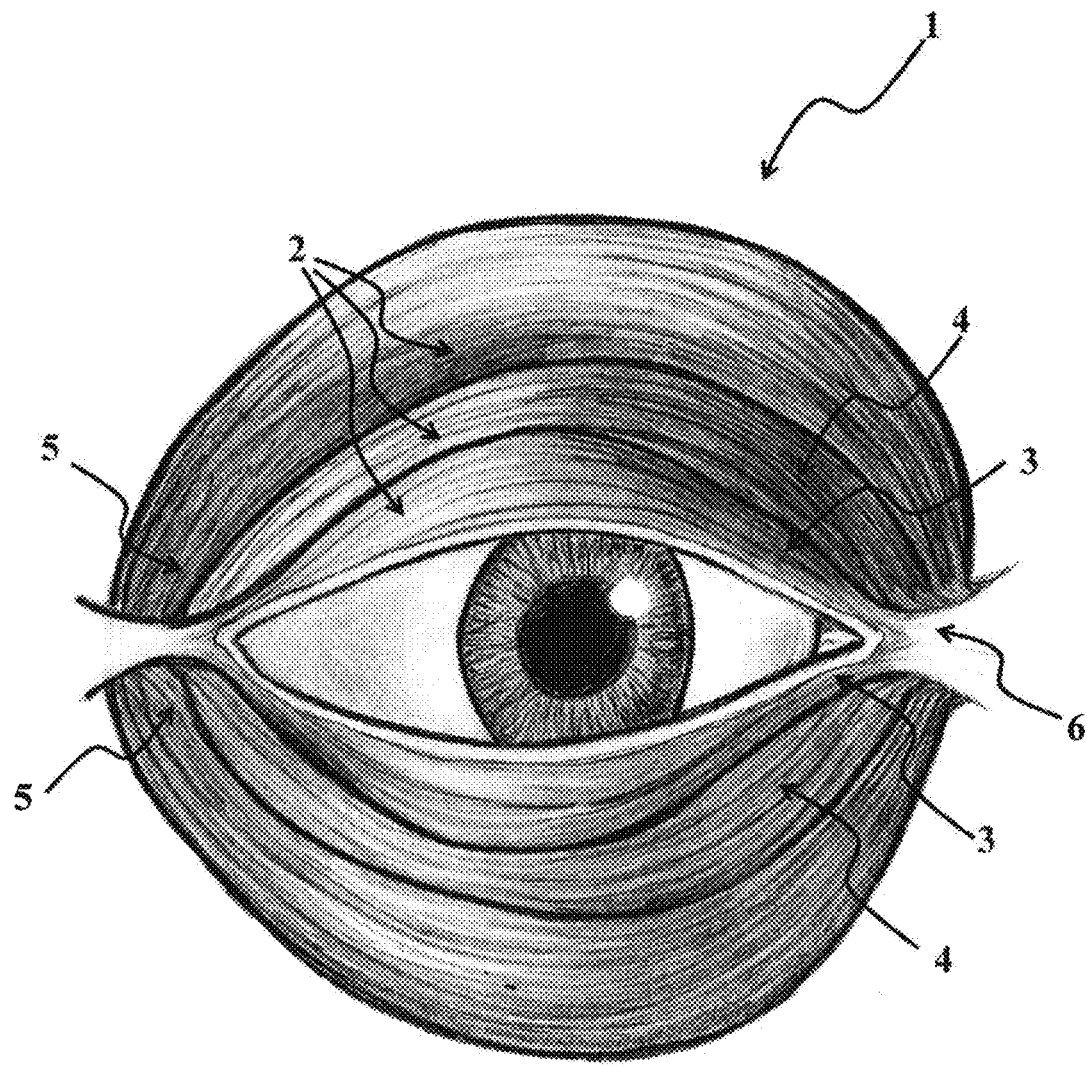
FIG. 1 is as illustration of the orbicularis muscle with pretarsal, preseptal and orbital components; the superficial heads of all three components insert into the medial canthal tendon.

Reference will now be made in detail to embodiments of the invention, examples of which are illustrated in the accompanying drawings. The terminology used in the description of the invention herein is for the purpose of describing particular embodiments only and is not intended to be limiting of the invention.

As used in the description of the invention and the appended claims, the singular forms "a", "an" and "the" are intended to include the plural forms as well, unless the context clearly indicates otherwise. The words "and/or" as used herein refers to and encompasses any and all possible combinations of one or more of the associated listed items. The words "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The words "right," "left," "lower" and "upper" designate directions in the drawings to which reference is made. The words "inwardly" and "outwardly" refer to directions toward and away from, respectively, the geometric center of the eyelid system, and designated parts thereof. The terminology includes the words noted above, derivatives thereof and words of similar import.

The following description is directed towards various embodiments of a medial canthoplasty and orbicularisorrhaphy performed in accordance with the present invention.

Figure 2:
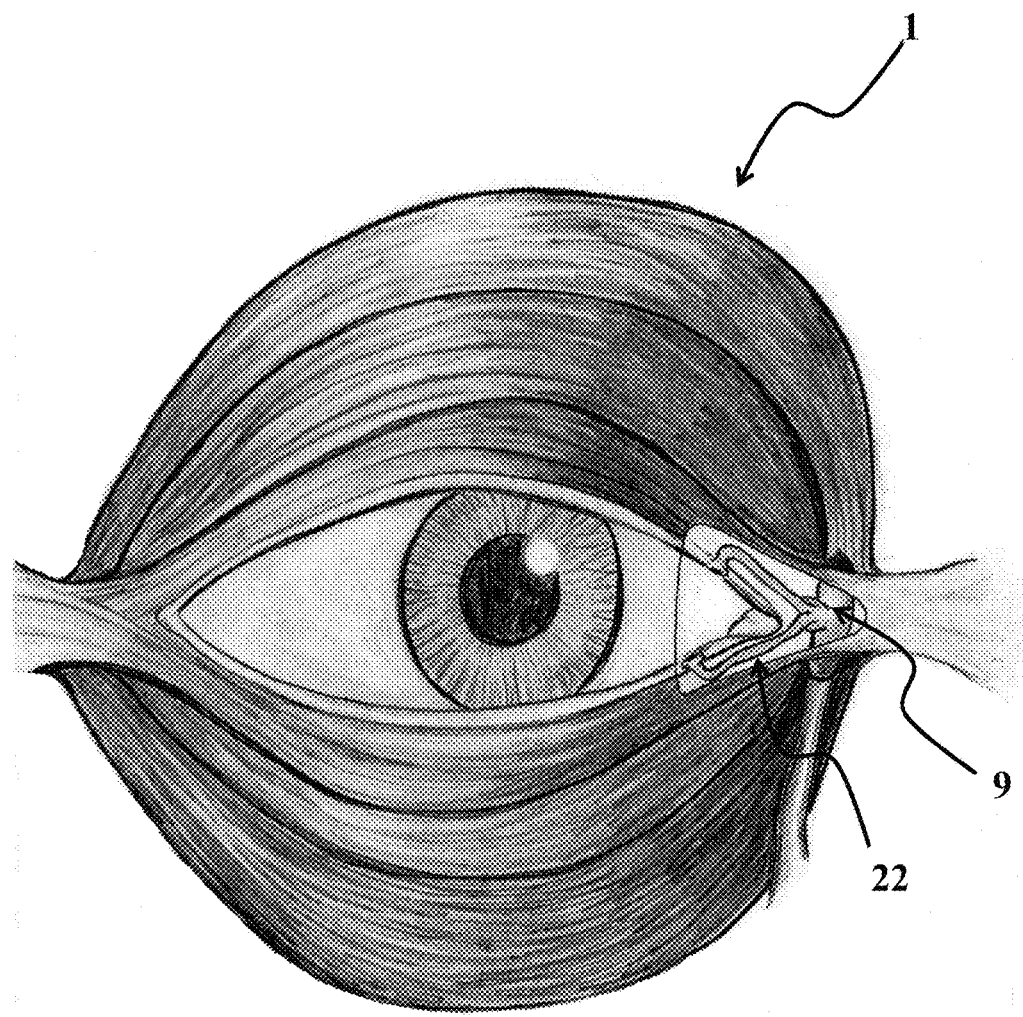
FIG. 2 shows a partially dissected view of the medial upper and lower eyelids, the pretarsal orbicularis having been excised medially to show the lacrimal system which lies underneath.
Figure 3:
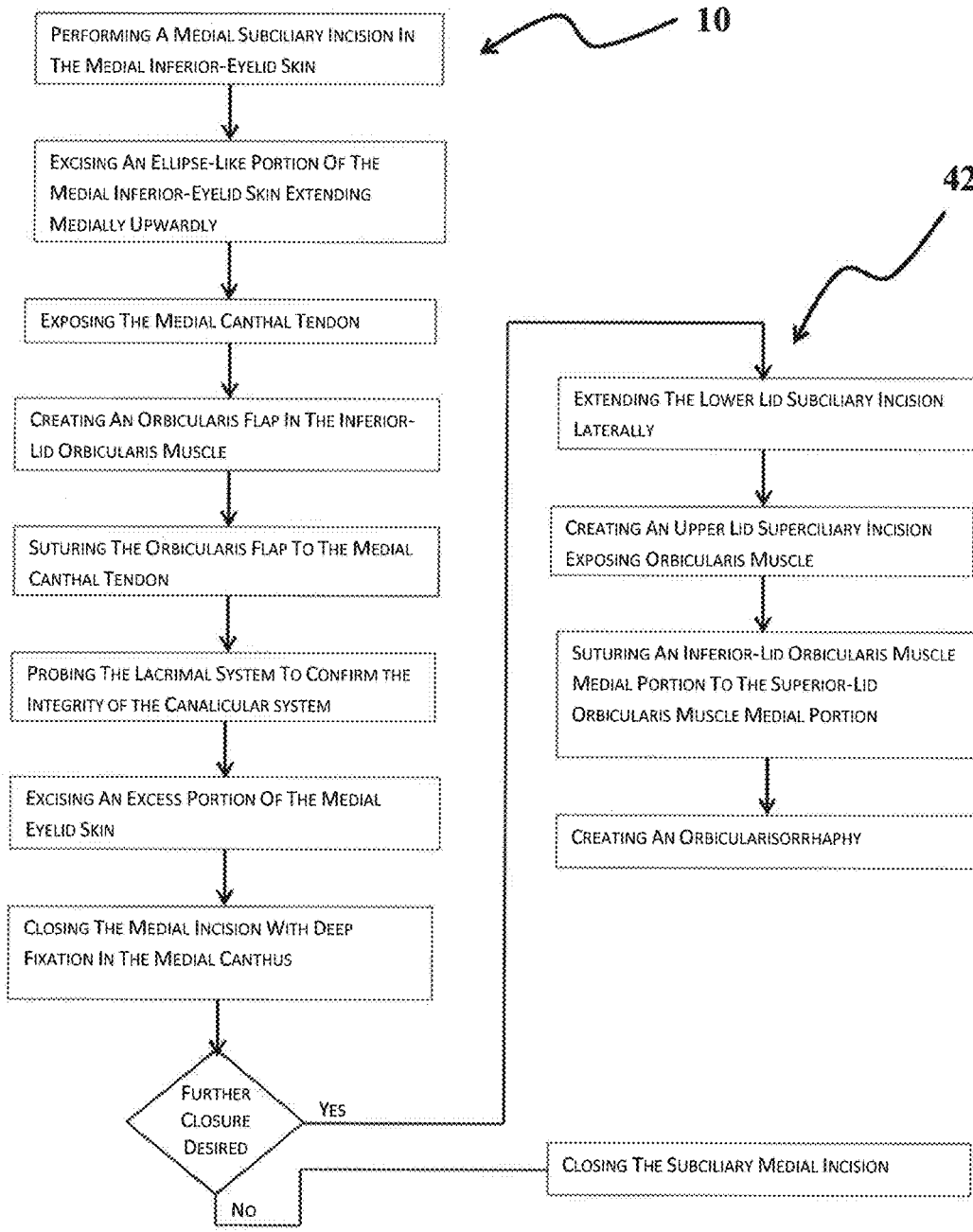
FIG. 3 flow diagram of the procedure

Referring to the drawings in detail, where like numerals indicate like elements throughout, there is shown in FIGS. 1 and 2 the dissected anatomy of the eyelid system 1. The orbicularis muscle 2 has pretarsal 3, preseptal 4 and orbital components 5. The superficial heads of all three components 3, 4, 5 insert into the medial canthal tendon 6. A partially dissected view of the medial upper 7 and lower eyelids 8 are shown (see, FIG. 2). The pretarsal orbicularis 3 has been excised medially to show the lacrimal system 9 which lies underneath.

FIGS. 3-10 show a first preferred embodiment of the surgical ophthalmic procedure, generally designated 10, for performing a medial cantholasty with an orbicularis flap and hereinafter referred to as the "medial orbicularis flap canthoplasty" 10 in accordance with the present invention.

The medial orbicularis flap canthoplasty 10 and orbicularisorrhaphy 42 are directed to an eyelid system 1 comprising an inferior (or lower) eyelid 12 with a medial inferior-eyelid skin 14, a superior (or upper) eyelid 16 with a medial superior-eyelid skin 18, a medial canthal tendon 6, an inferior-lid orbicularis muscle 20, a superior eyelid orbicularis muscle and a canalicular system 22.

Figure 11:
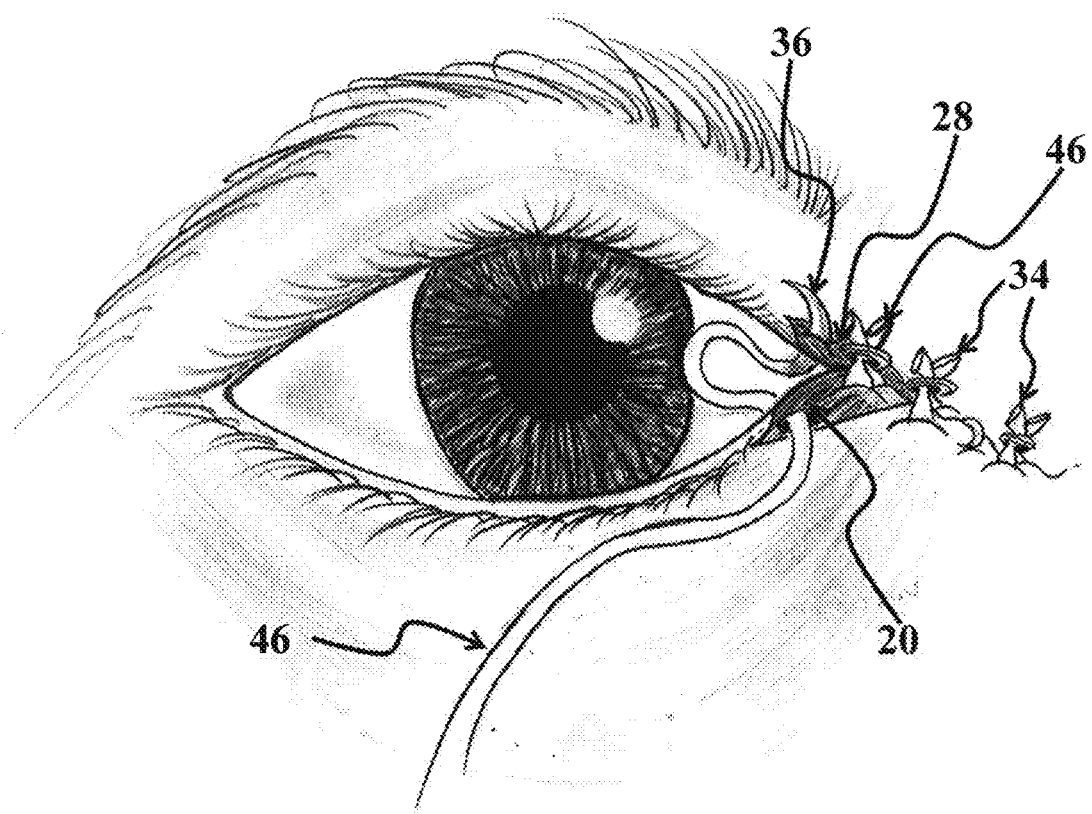
FIG. 11 shows the suturing of the lower lid orbicularis to the upper lid orbicularis thus performing an orbicularisorrhaphy in accordance with a preferred embodiment of the present invention.
Figure 12:
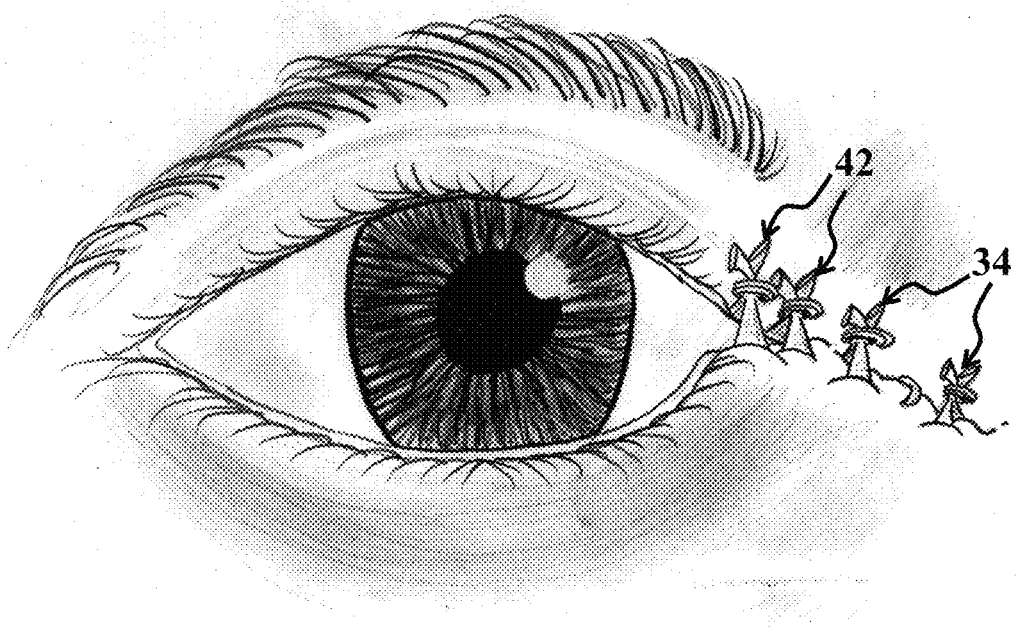
FIG. 12 shows the completed procedure with the medial lid raised and tightened with orbicularissorhaphy and skin sutures in place.

The purpose of the medial orbicularis flap canthoplasty 10 is to shorten the medial aspect of the inferior eyelid 12. This is done by connecting an orbicularis flap 24 to the medial canthal tendon 6 (see, FIGS. 5-7) as further described below. Referring to FIGS. 11 and 12, if necessary a form of tarsorrhaphy referred to hereafter as an "orbicularisorrhaphy" 42 is performed where the inferior eyelid orbicularis muscle 20 of the inferior eyelid 12 is sutured to the superior eyelid orbicularis 28 of the superior eyelid 16.

Figure 4:
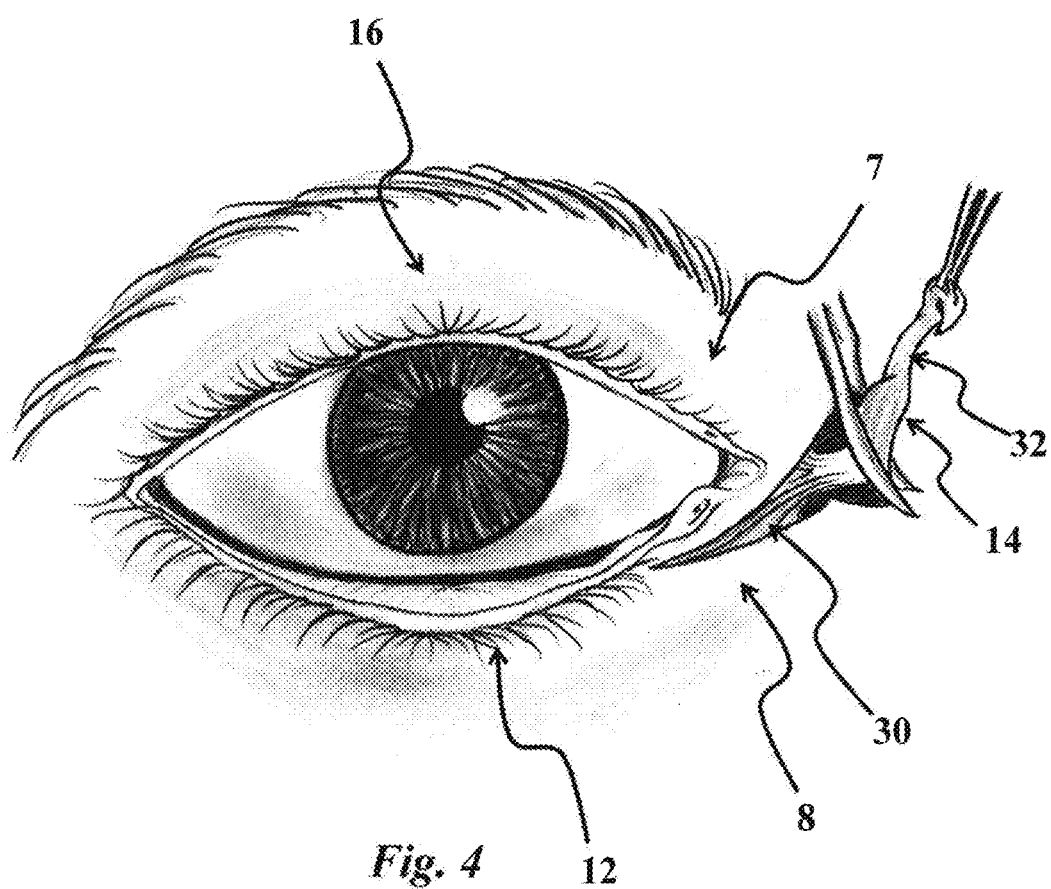
FIG. 4 shows the subciliary incision performed and the skin flap excised in accordance with a preferred embodiment of the present invention to visualize and tighten the medial canthus.
Figure 5:
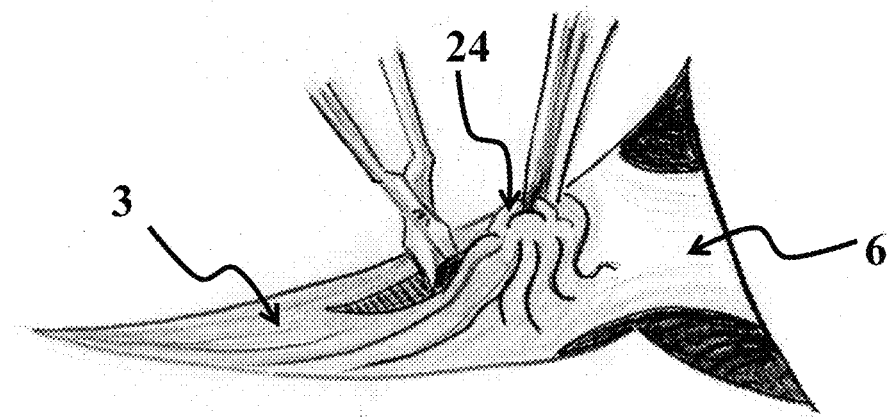
FIG. 5 shows an orbicularis flap, of a thickness sufficient to create a new medial canthal tendon, being created from the pretarsal orbicularis in accordance with a preferred embodiment of the present invention to visualize and tighten the medial canthus.
Figure 6:
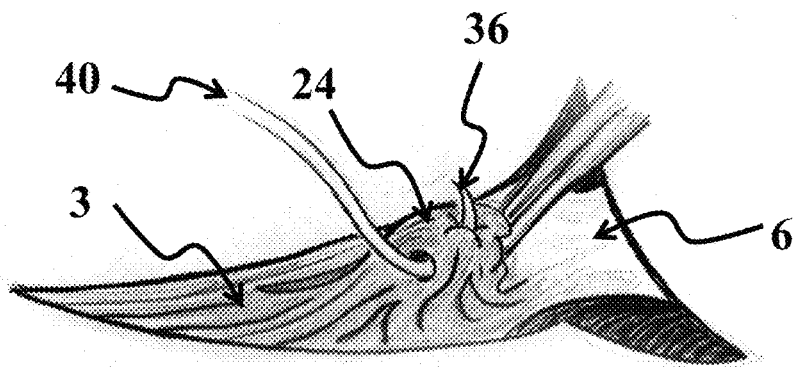
FIG. 6 shows a 5-0 vicryl suture being placed through the orbicularis flap as a first bite in accordance with a preferred embodiment of the present invention.
Figure 7:
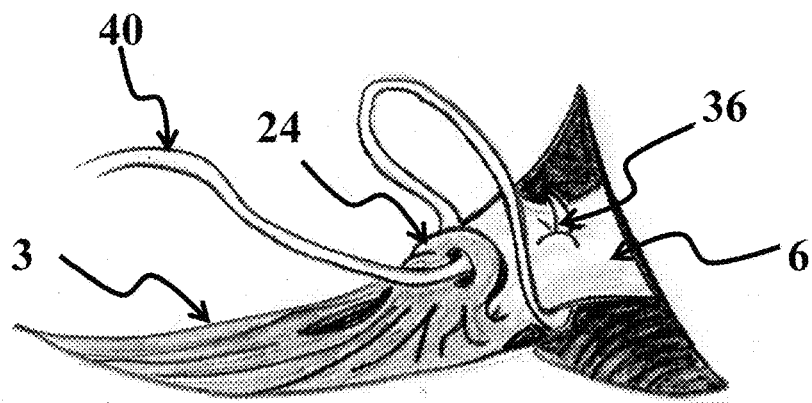
FIG. 7 shows the 5-0 vicryl suture of FIG. 8 being placed into medial canthal tendon as a second bite in accordance with a preferred embodiment of the present invention.
Figure 8:
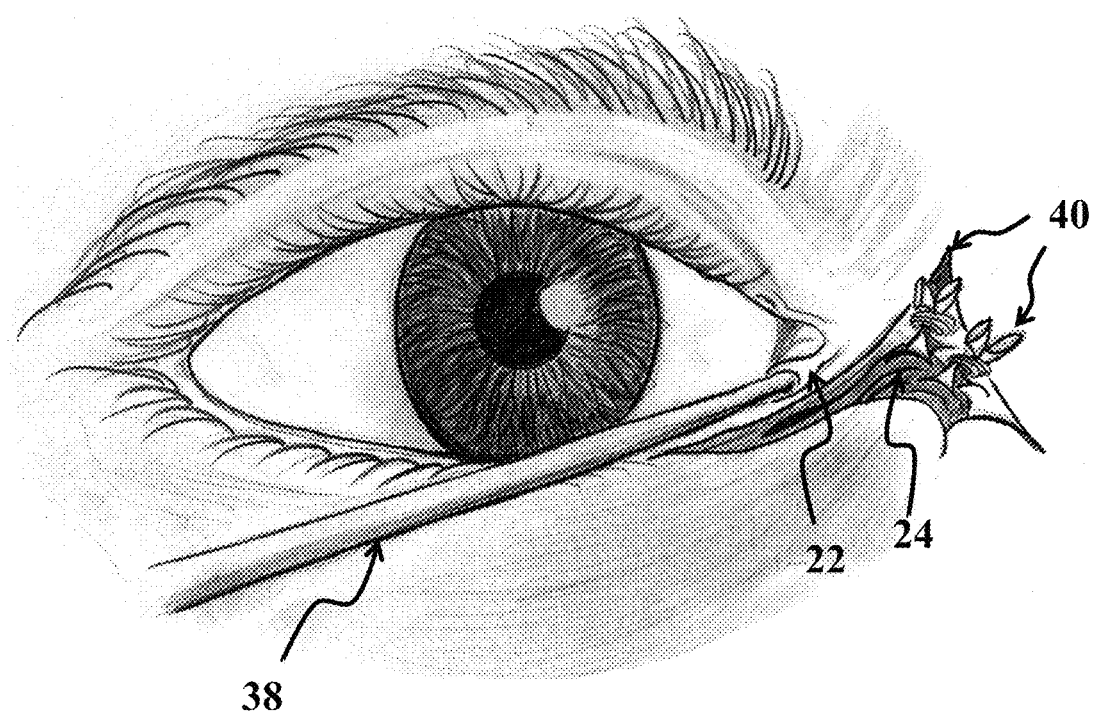
FIG. 8 shows the orbicularis flap sutured and tied tightening the lid to the medial canthal tendon, raising and apposing the lid and the puncta closer to the globe. It also shows the probing of the lower canaliculus to make sure it is not damaged when the medial orbicularis tightening is performed in accordance with a preferred embodiment of the present invention.
Figure 9:
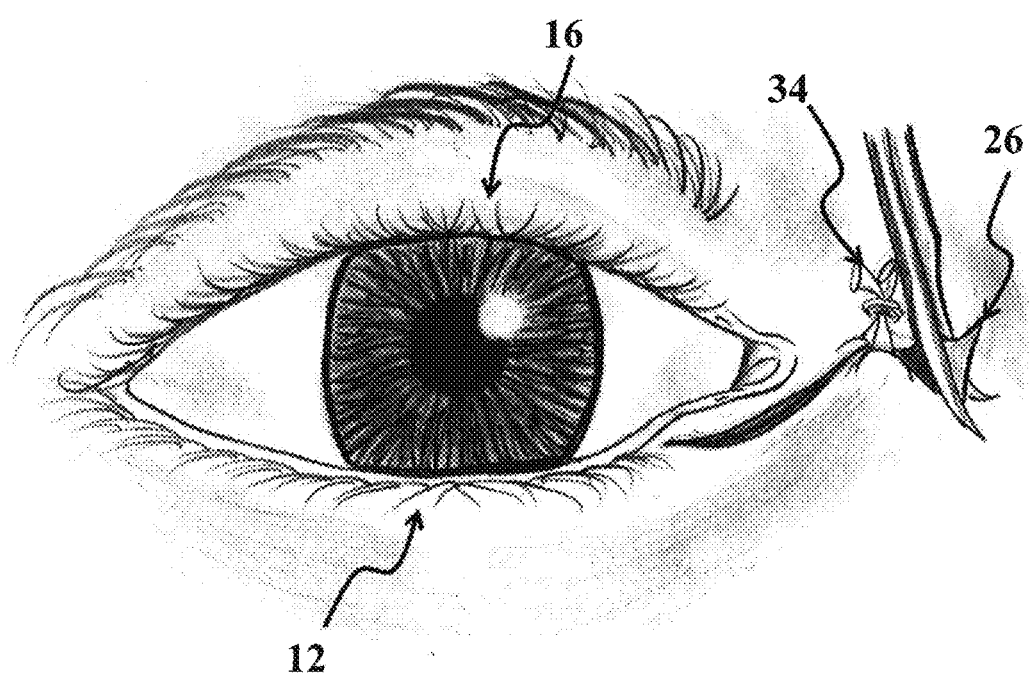
FIG. 9 shows the excess skin triangle being excised in accordance with a preferred embodiment of the present invention.
Figure 10:
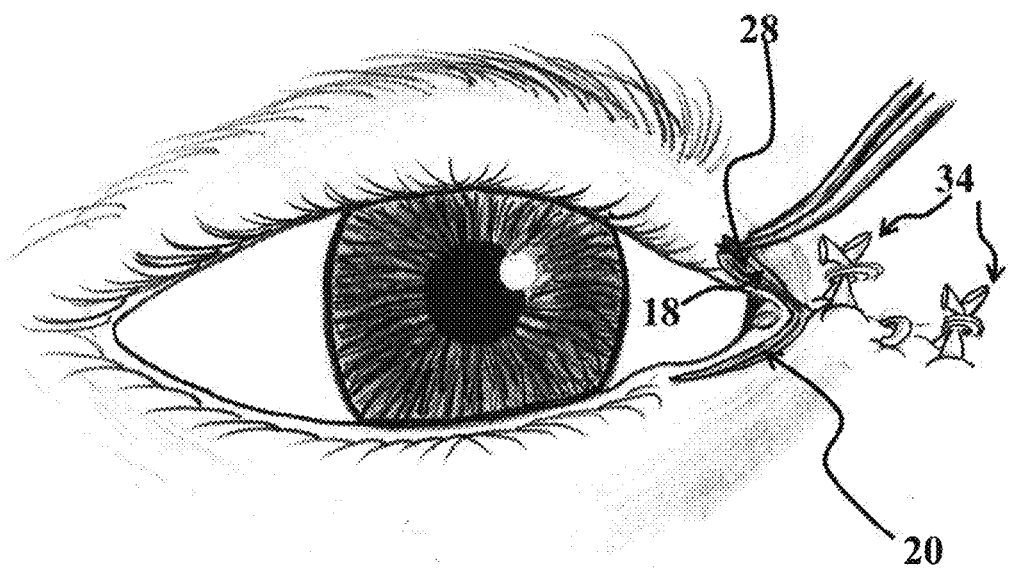
FIG. 10 shows further skin fixation using deep 5-0 vicryl sutures in accordance with a preferred embodiment of the present invention. It also shows an extension of the incision medially in the subciliary lower and supraciliary upper lid to expose the orbicularis which can then be sutured together to further close the inner aspect of the lid in accordance with a preferred embodiment of the present invention.

Referring to FIG. 4, after standard pre-operative practice directed to preparation of the surgical site, the medial orbicularis flap canthoplasty 10 begins by performing a medial subciliary incision 30 in the medial inferior-eyelid skin 14.

A portion 32 of the medial inferior-eyelid skin extending medially upwardly is excised (see, FIG. 4). The dissection is continued inferiorly creating the orbicularis flap 24 (see, FIG. 5) that will be reattached to the medial canthal tendon 6. The orbicularis flap 24 is undermined to confirm detachment of the flap from the medial inferior-eyelid skin 14 and that the flap does not create canalicular distortion. A suture 40, preferably 5-0 vicryl, and a P-2 needle 36 are placed first through the orbicularis flap 24 (see, FIG. 6) and then underneath and through the medial canthal tendon 6 (see, FIG. 7). When the suture 40 is tightened, the suture 40 raises and tightens the medial inferior eyelid 8 (see, FIG. 7).

Additional sutures 40 may be placed to reinforcingly attach the orbicularis flap 24 to the canthal tendon 6. (see, FIG. 8). In some embodiments the canalicular system 22 is probed with a Bowman probe 38 to assure that the canalicular system 22 is open and will not be sutured into. The medial eyelid skin 14 is sutured with a 5-0 vicryl suture 34 with deep fixation to the medial canthal tendon 6 in order to raise the medial inferior eyelid 8, creating a small triangle of excess eyelid skin 26 which is excised (see, FIG. 9). When the procedure is completed, the canaliculi is probed or irrigated to assure that there is no damage to the canaliculi.

Referring to FIGS. 11 and 12, in some embodiments of the medial orbicularis flap canthoplasty 10, when further medial closure of the eye is desired, an orbicularisorrhaphy 42, a medial alternative to a lateral tarsorrhaphy, is performed prior to the closing step. In contrast to a lateral tarsorrhaphy in which the tarsus of the lower lid is sutured to the tarsus of the upper lid, medially, this is not possible as the lower tarsus ends at the puncta and is not present medial to the puncta. Accordingly, during the orbicularisorrhaphy 42, an inferior-lid orbicularis muscle medial portion is sutured with an orbicularisorrhaphy suture 46 to the superior-lid orbicularis muscle medial portion to obtain the desired closure.

Figure 13:
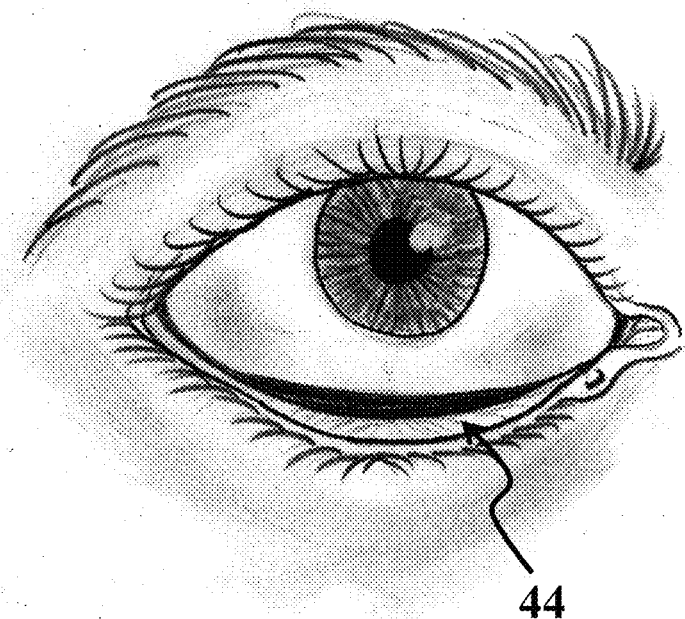
FIG. 13 shows a pre-operative drawing of an ectropic lid, more so medially.
Figure 14:
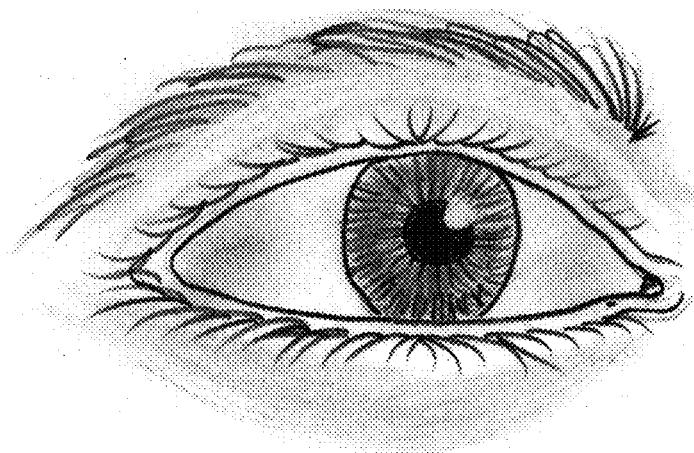
FIG. 14 shows the post-operative result of the canthoplasty performed in accordance with a preferred embodiment of the present invention with excellent apposition to the globe.

A pre-operative drawing of an ectropic lid 44, more so medially, is shown in FIG. 13 and the post-operative result of the medial orbicularis flap canthoplasty with orbicularisorrhaphy performed in accordance with a preferred embodiment of the present invention with excellent apposition to the globe is shown in FIG. 14.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The features designated by the reference numbers appearing in the drawings and cited in the foregoing description are identified in the following table:

| Table of Reference Numbers | |
|---|---|
| No. | Description |
| 1. | Eyelid System |
| 2. | Orbicularis muscle |
| 3. | Pretarsal orbicularis muscle |
| 4. | Preseptal orbicularis muscle |
| 5. | Orbital orbicularis components |
| 6. | Medial canthal tendon |
| 7. | Medial upper eyelid |
| 8. | Medial lower eyelid |
| 9. | Lacrimal system |
| 10. | Medial orbicularis flap canthoplasty |
| 12. | Inferior (or lower) eyelid |
| 14. | Medial inferior-eyelid skin of 12 |
| 16. | Superior (or upper) eyelid |
| 18. | Supraciliary incision exposing pretarsal orbicularis muscle |
| 20. | Inferior eyelidlid orbicularis muscle |
| 22. | Canalicular system |
| 24. | Orbicularis flap |
| 26. | Excess eyelid skin |
| 28. | Superior eyelid orbicularis muscle |
| 30. | Medial subciliary incision |
| 32. | Ellipse-like portion of the medial inferior-eyelid skin |
| 34. | Skin Suture |
| 36. | P-2 needle |
| 38. | Bowman probe |
| 40. | Orbicularis flap suture - orbicularis flap to medical canthal tendon |
| 42. | Orbicularisorrhaphy |

-continued

Table of Reference Numbers

| No. | Description |
|---|---|
| 44. | Ectropic lid |
| 46. | Orbicularisorrhaphy suture - superior to inferior orbicularis |

I claim:

1. A surgical ophthalmic procedure for performing a medial canthoplasty of an eyelid system comprising an inferior eyelid with a medial inferior-eyelid skin, a superior eyelid with a medial superior-eyelid skin, a medial canthal tendon, an inferior-lid orbicularis muscle, a lacrimal system and a canalicular system, the surgical ophthalmic procedure comprising the steps of:

performing a medial subciliary skin incision in the medial inferior-eyelid skin;

excising a portion of the medial inferior-eyelid skin extending medially upwardly;

exposing the medial canthal tendon;

creating an orbicularis flap in the inferior-lid orbicularis muscle;

suturing the orbicularis flap to the medial canthal tendon;

probing the lacrimal system to confirm an integrity of the canalicular system;

excising an excess portion of the medial superior-eyelid skin; and closing the medial inferior-eyelid skin with deep fixation in the medial canthal tendon closing the medial subciliary skin incision.

2. The surgical ophthalmic procedure according to claim 1, wherein the eyelid system further comprises a superior-lid orbicularis muscle having a superior-lid orbicularis muscle medial portion and the surgical ophthalmic procedure further comprises an orbicularisorrhaphy suturing an inferior-lid orbicularis muscle medial portion to a superior-lid orbicularis muscle medial portion.

* * * * *